United States Patent [19]

Yamauchi et al.

[11] 4,019,226
[45] Apr. 26, 1977

[54] APPARATUS FOR AUTOMATICALLY SHAPING CELLULOSE TYPE MENSTRUAL TAMPONS

[75] Inventors: Akira Yamauchi, Hyogo; Tetsu Kakuma, Kashiwara; Hisao Yamashita, Kawanishi; Masahiko Ariga, Takatuski, all of Japan

[73] Assignee: Jex Co., Ltd., Osaka, Japan

[22] Filed: Jan. 15, 1975

[21] Appl. No.: 541,128

Related U.S. Application Data

[63] Continuation-in-part of Ser. No. 302,542, Oct. 31, 1972, abandoned.

[30] Foreign Application Priority Data

Aug. 10, 1972 Japan .............................. 47-80615

[52] U.S. Cl. ............................................. 19/144.5
[51] Int. Cl.² ........................................ A61L 15/00

[58] Field of Search .................. 19/144.5, 145, 149

[56] References Cited

UNITED STATES PATENTS

| | | | |
|---|---|---|---|
| 2,763,899 | 9/1956 | Niepmann et al. ............... | 19/144.5 |
| 2,977,644 | 4/1961 | Wieser ........................... | 19/144.5 X |
| 3,852,847 | 12/1974 | Etz ................................. | 19/144.5 |

*Primary Examiner*—Dorsey Newton
*Attorney, Agent, or Firm*—Hall & Houghton

[57] ABSTRACT

An apparatus for automatically shaping cellulose type menstrual tampons with all the operational steps being automated wherein a cotton band used as a stock material is processed therein until a product of cocoon-like final shape suitable for use as a menstrual tampon is produced.

8 Claims, 27 Drawing Figures

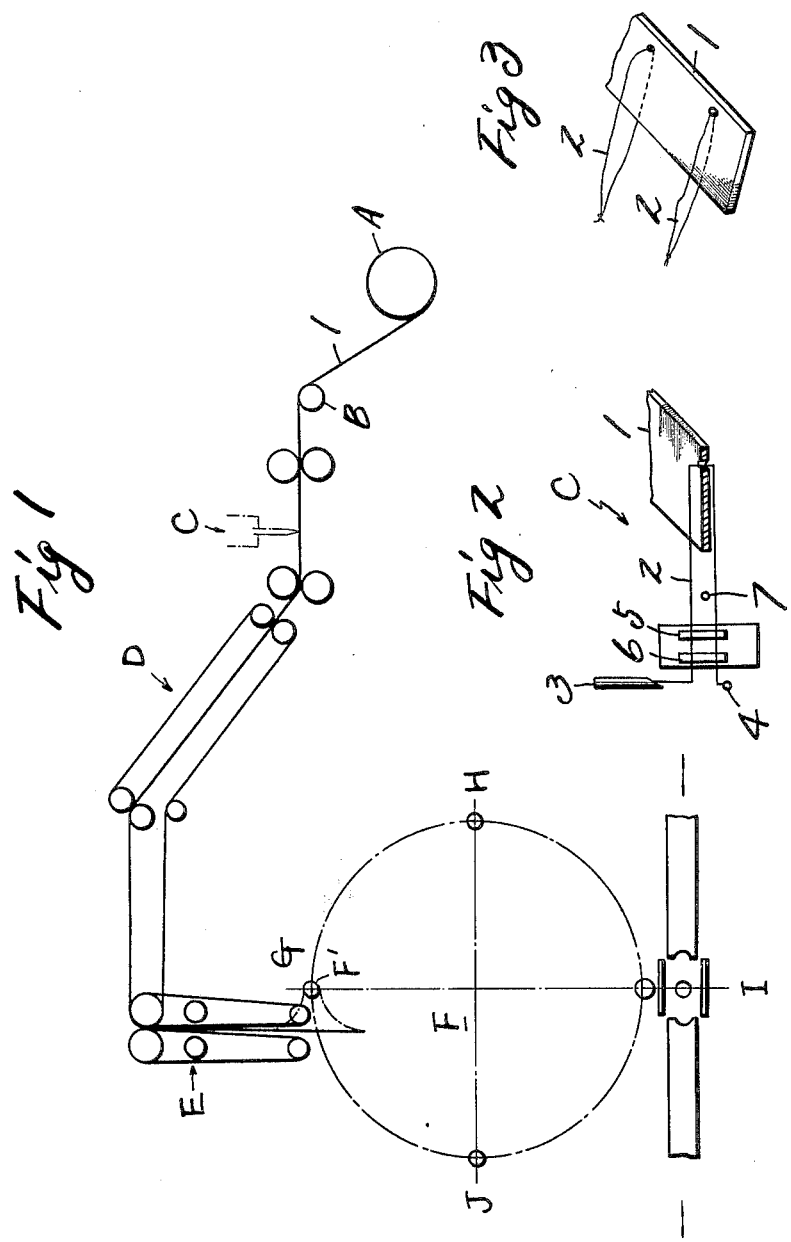

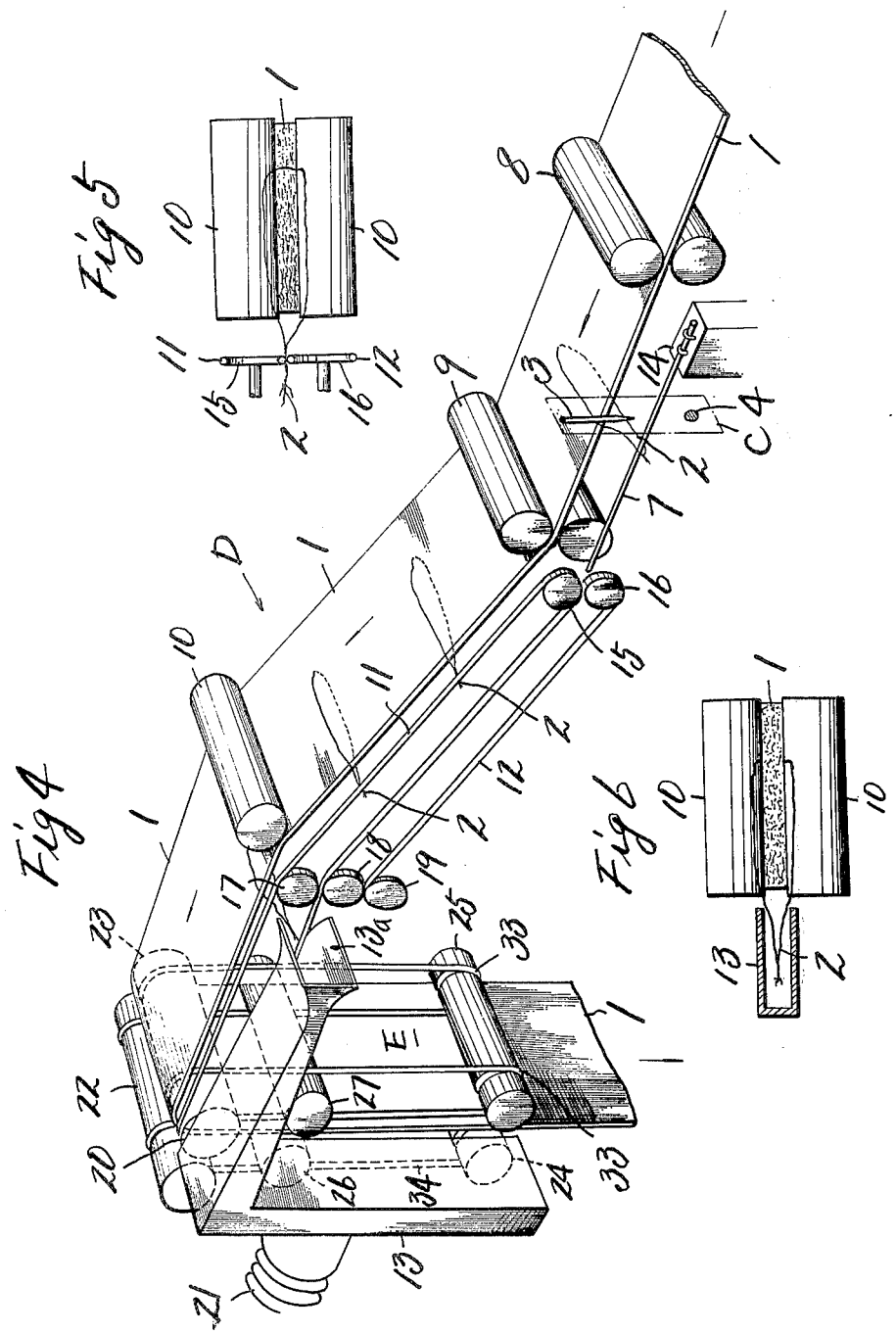

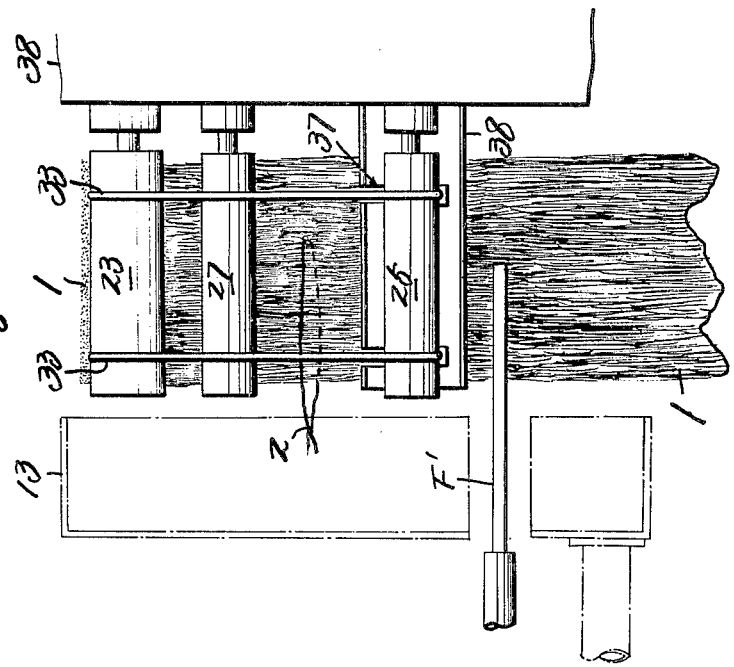
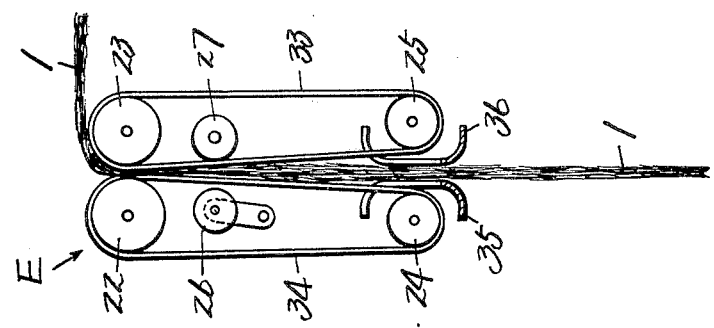

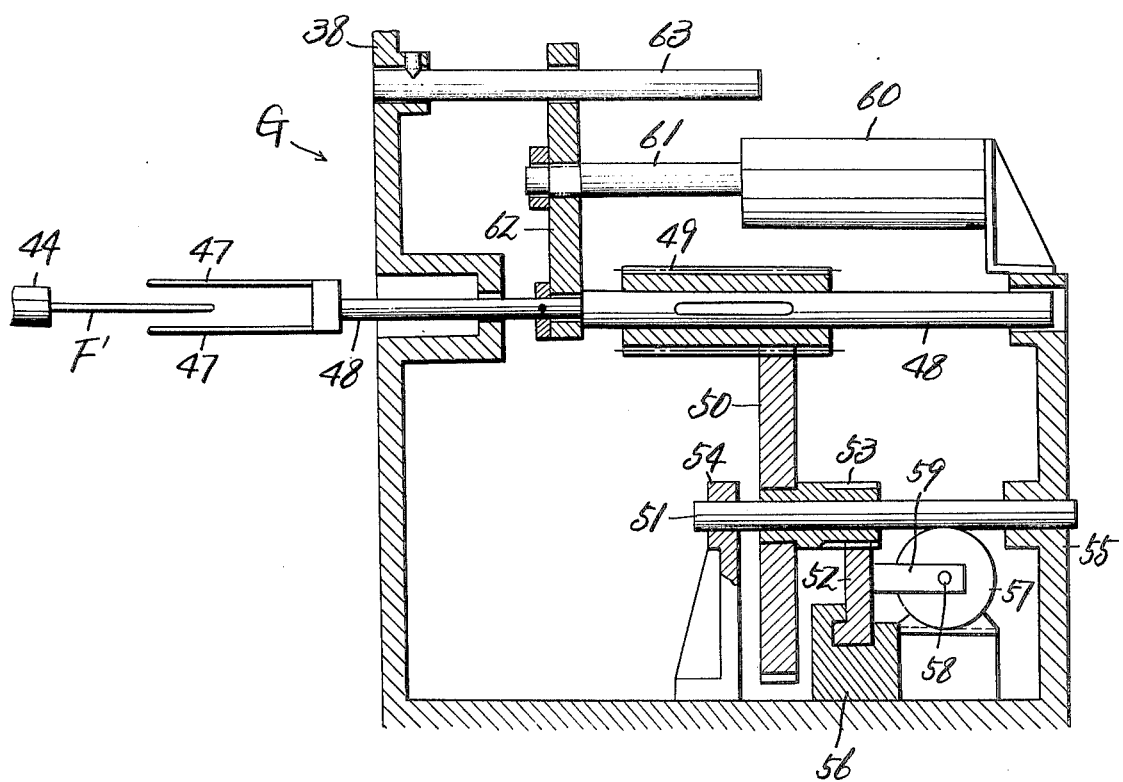

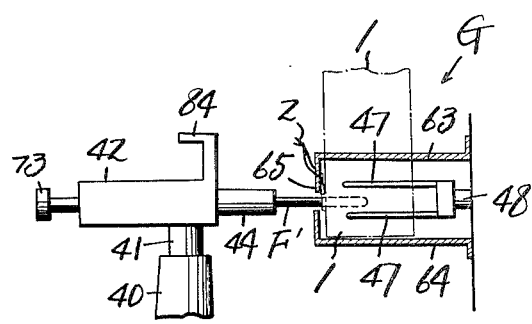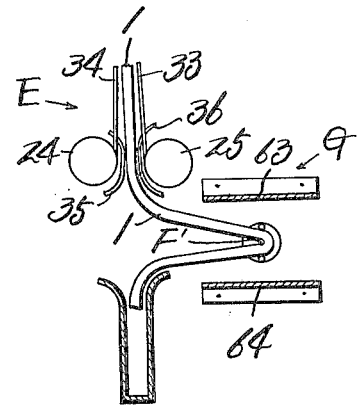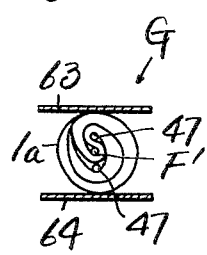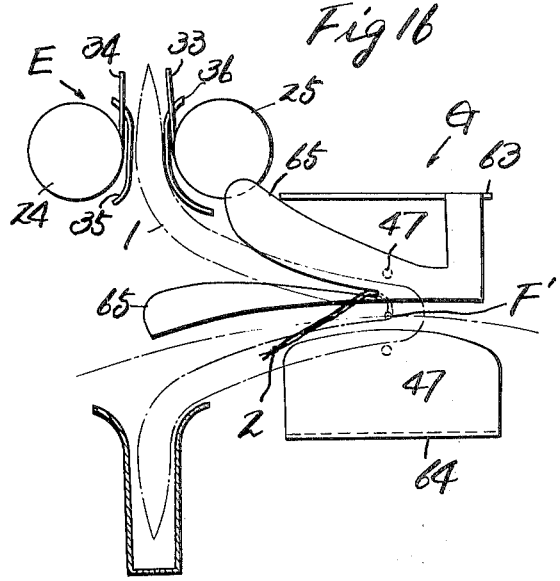

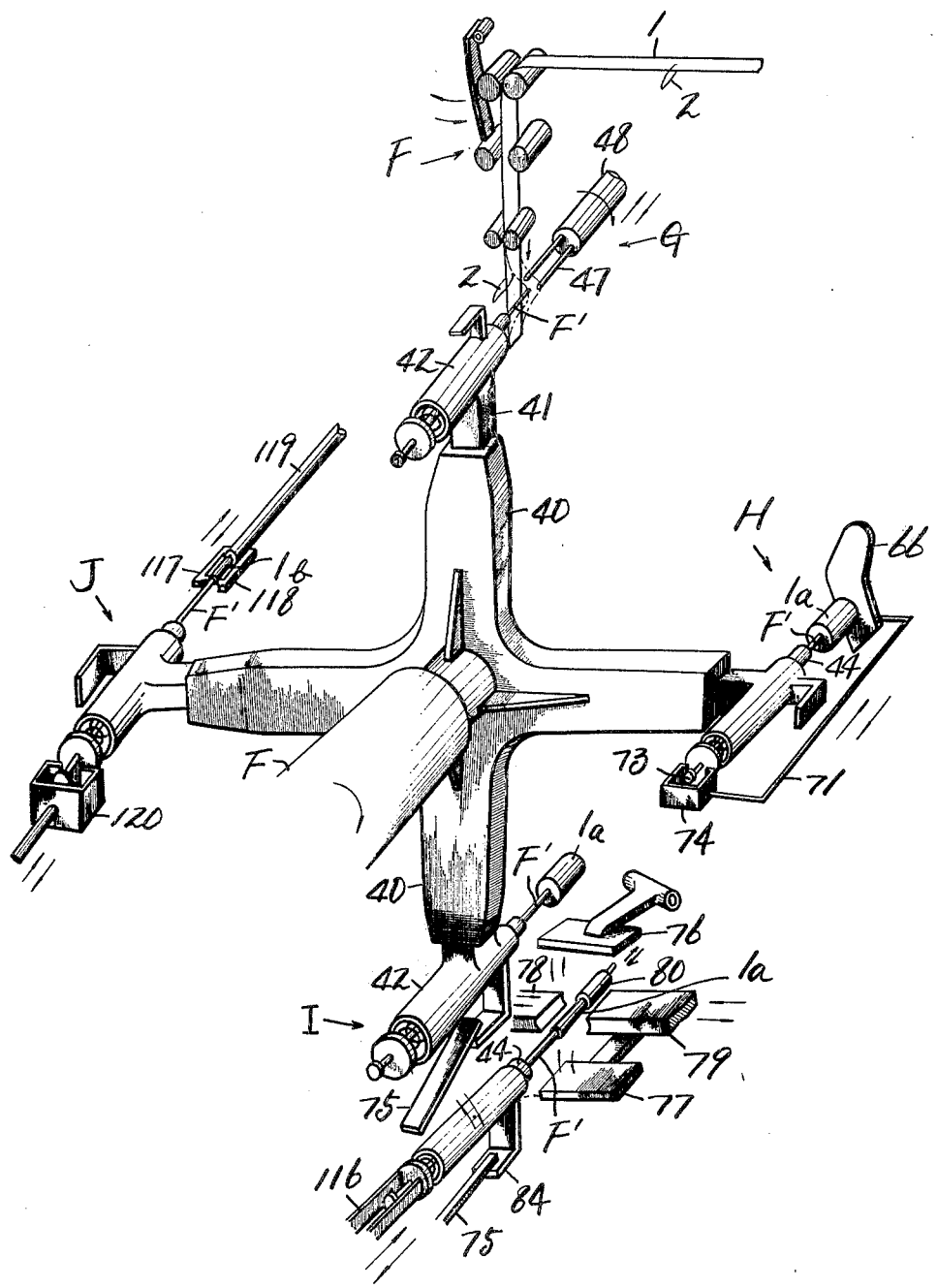

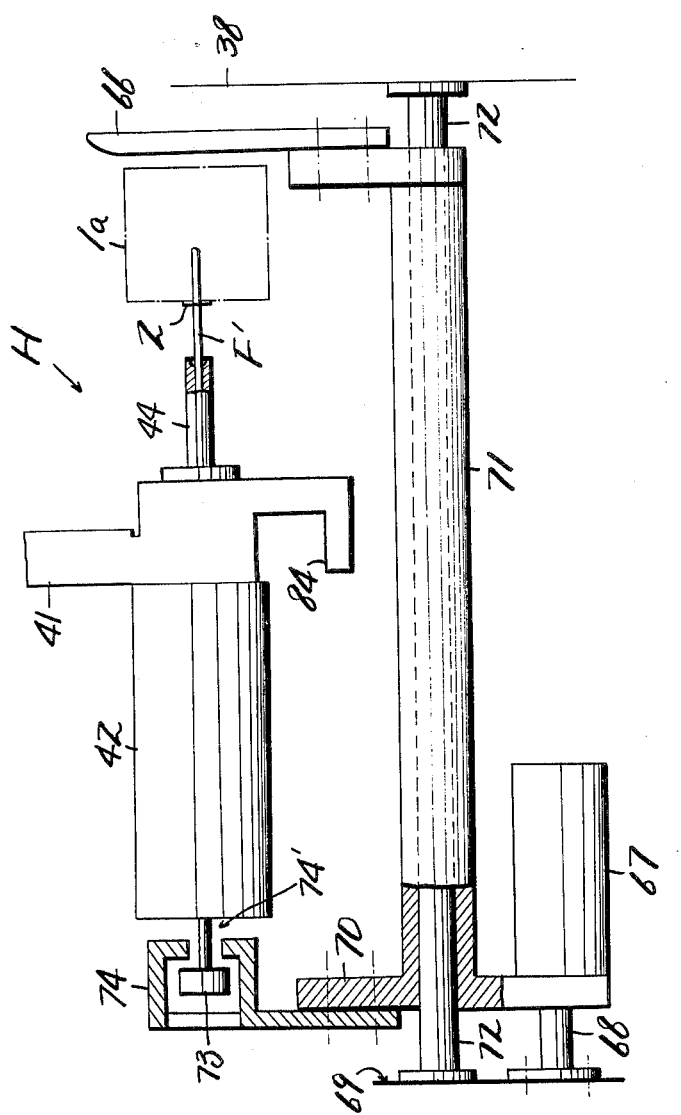

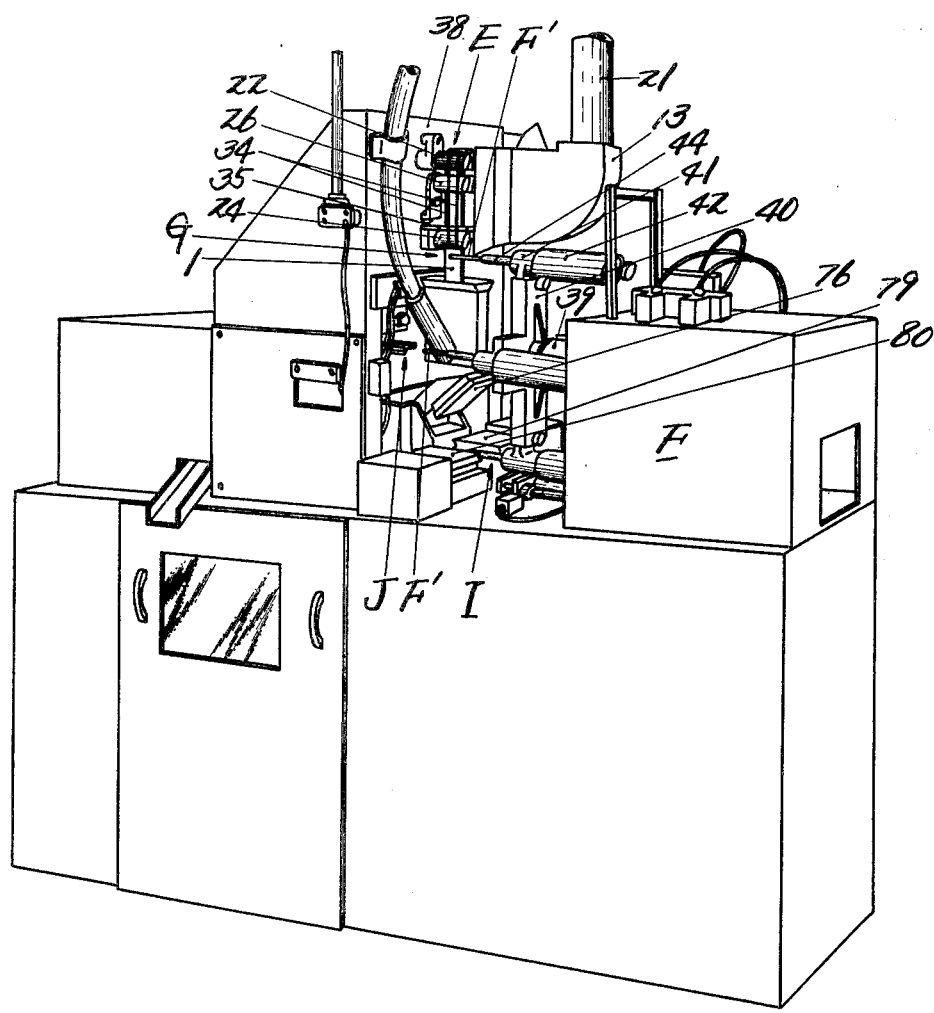

APPARATUS FOR AUTOMATICALLY SHAPING CELLULOSE TYPE MENSTRUAL TAMPONS

RELATED APPLICATION

This application is a continuation-in-part of our co-pending application Ser. No. 302,542, filed Oct. 31, 1972, now abandoned.

BACKGROUND OF THE INVENTION

1. Field of the Invention

The present invention relates to an apparatus for automatically shaping stock material in the form of a cotton band to produce cellulose type menstrual tampons.

2. Field of the Prior Art

Heretofore, in the production of cellulose type menstrual tampons a method has been employed in which cotton fiber band is cut into suitable lengths required by the tampon, a string is thereafter attached to the cut cotton fiber article and the fiber article then compressed into a cocoon shape to produce the tampon. However, since almost all the steps are manually carried out, the rate of production is very low. Moreover, such a method is not a desirable one from a standpoint of health and hygiene.

SUMMARY OF THE INVENTION

An object of the present invention is to provide apparatus which will make it possible to fully automate the production of tampons on a continuous basis, thereby greatly increasing the rate of production and to eliminate any problems with respect to hygiene.

Another object of the present invention is to provide apparatus having means to break the continuous cotton fiber stock or band at opposite break ends by tearing it off into lengths, with each being of the length required by one tampon article. The purpose of providing such break ends is to facilitate, when the cotton fiber article is used in the form of a wound roll, the twining of the break ends around the periphery of the roll of the cotton fiber article and to thereby avoid a change in the thickness of the cotton fiber article, such as the formation of a shoulder therein. Further, this procedure ensures that when a roll of cotton fiber band is compressed into a cocoon shape to produce the desired tampon product, the tampon product will possess a smooth outer peripheral surface resulting in a perfect fit in the tampon product when same is used.

A further object of the present invention is to successfully guide a withdrawing string so as to embed it in the cotton fiber band in such a manner that it is present on one side of the tampon product thereby facilitating the withdrawal of the tampon when in use, and to also result in the automatically taking out of the apparatus the finally compressed shape tampon product without destroying its configuration.

BRIEF DESCRIPTION OF THE DRAWINGS

FIG. 1 is a layout view of the component stations making up the apparatus made in accordance with the present invention.

FIG. 2 is an enlarged perspective view of the string attaching station of the apparatus made in accordance with the present invention.

FIG. 3 is an enlarged perspective view of the withdrawing strings in their attached position on the cotton fiber band.

FIG. 4 is an enlarged perspective view of the component means of the apparatus for feeding and guiding the cotton fiber band or stock and a withdrawing string.

FIG. 5 is an enlarged front view showing a withdrawing string being transferred by means of rubber belts at the feeding and guiding station of the apparatus.

FIG. 6 is a front view showing a withdrawing string being transferred by means of a suction nozzle at the feeding and guiding station.

FIG. 7 is a front view of means for breaking the cotton fiber band or stock into individual cotton fiber articles.

FIG. 8 is a side view of the breaking means shown in FIG. 7.

FIG. 12 is a sectional view of a form of mechanism for driving the winding means of the winding station of the present apparatus.

FIG. 13 is a side view showing the relation between the turret spindle station and the winding means station of the apparatus of the present invention.

FIG. 14 is a front view of the mechanism shown in FIG. 13.

FIG. 15 is a front view showing the cotton fiber article in its wound state.

FIG. 16 is a front view of a winding guide for the withdrawing strings at the winding station.

FIG. 17 is an enlarged fragmentary schematic perspective view showing the manner of operation of the turret machine at the individual stations thereof.

FIG. 18 is an enlarged side view of a string fixing station of the apparatus of the present invention.

FIG. 27 is a perspective rear view of the machine shown in FIG. 26.

DESCRIPTION OF THE PREFERRED EMBODIMENT

Figure 10:
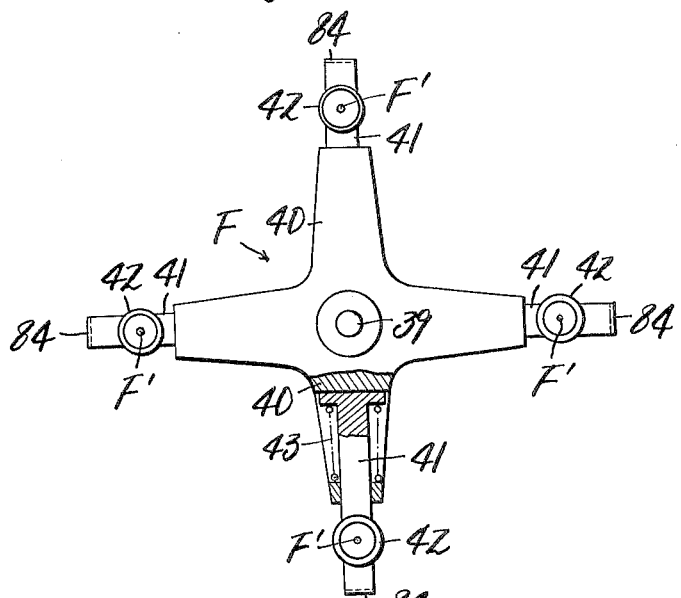
FIG. 10 is a front view of a turret head station forming a part of the apparatus.

Referring now to FIG. 1, it is seen that long continuous cotton fiber band or stock, designated by reference numeral 1, is drawn from a cotton reel A and passed over a guide roller B to a string attaching means, designated by reference letter C. Withdrawing strings 2 are attached to the fiber cotton fiber band at suitable intervals, after which the cotton fiber band 1 is then passed through the feeding and guiding station D and then to the breaking station E, where the cotton fiber band 1 is broken into suitable length, such length being that required by one tampon article. The individual cotton fiber bands 1 are then arrested by the spindles F' of a turret machine station F and thereafter wound by winding means G at a first winding station, with the wound string being then embedded in one end of each of the individual cotton fiber bands at a second station H to produce a wound cotton fiber article 1a. At a third station compression shaping means I compressively shapes each of the wound cotton articles 1a into a tampon of the desired predetermined columnar shape, and at a fourth station the formed tampon is pulled out of the spindle by discharge means J and collected in a product receiver or the like. This description sets forth the basic component parts of the apparatus of the present invention.

The string attaching means or station C, as shown in FIG. 2, comprises a hollow needle rod through which the withdrawing string 2 drawn from a suitable bobbin or the like is passed, with a string end arresting body 4 being provided which is opposed thereto. Thus, in the string attaching operation the needle rod and the string and arresting body are moved horizontally to positions above and below the cotton fiber band 1 respectively. The needle rod 3 is then lowered to pierce the fiber band cotton 1 and the string end arresting body 4 arrests the string end, whereupon the needle rod 3 is lifted and laterally moved away from the fiber cotton 1. A string knotter 5 is provided which effects the knotting of the string and a cutter 6 is also provided to cut the string end. In this way, the tampon withdrawing strings 2 are attached to the cotton fiber band 1 at regular intervals, as shown in FIG. 3. In addition, as shown in FIG. 2 the numeral 7 designates a guide wire for use with the withdrawing strings 2.

Referring now to FIG. 4, the feeding and guiding means or station D of the overall apparatus serves to feed the long continuous cotton fiber band 1 having the withdrawing strings 2 which have been attached thereto at regular intervals by the string attaching means or station C into the breaking means or station E, which will be described more fully hereinafter, with respect to several pairs of cotton feed rollers 8, 9 and 10, and includes means which will ensure that the withdrawing strings 2 will be guided and fed without being caught. That is, means are so provided that the withdrawing strings 2 are pulled outwardly toward one side of the fiber cotton 1 and are held between and conveyed by two rubber belts 11 and 12, as shown in FIG. 5, while the strings 2 are being sucked to one side by a suction nozzle 13, as shown in FIG. 6.

The guide wire 7 described above is provided in order to prevent the withdrawing strings 2 from drooping or being folded back onto the cotton fiber band 1 during travel from the string attaching means or station C to the nip of the rubber belts 11 and 12. One end of the guide wire 7 is fixed to a machine frame portion 14 forwardly of the string attaching station C with the other end of the guide wire being in the form of a free end extending to the point of contact between pulleys 15 and 16 for the rubber belts 11 and 12. Thus, the withdrawing strings 2 attached at the string attaching station C are supported on the guide wire 7 and guided to the rubber belts 11 and 12, where they are held therebetween and then conveyed to and sucked by the suction nozzle 13, and then, along with the cotton fiber band 1, are guided and fed into the breaking means or station E for procession in a manner to be described more fully hereinafter.

One rubber belt 11 is entrained around pulleys 15, 17 and 20 and the other rubber belt is entrained around pulleys 16 and passes between pulleys 18 and 19. Upon rotation of the cotton feed rollers, the rubber belts 11 and 12 are rotated to advance the withdrawing strings 2 at the same rate of speed as that of the cotton fiber band 1. If desired, the rubber belts 11 and 12 may be omitted and in lieu thereof the suction nozzle 13 may be extended to the free end of the guide wire 7. The suction nozzle 13 is fixed in position so as to present its elongated opening along one side of the path of movement of the cotton fiber band 1 and is connected to any suitable suction generating means (not shown) through a duct 21. The inlet portion 13a of the suction nozzle 13 is flared so that the withdrawing strings 2 may not become hooked or improperly lodged therein. Further, the cross-section of the suction nozzle 13 is hollow and square shaped throughout a substantial length thereof, with one short side of the square being open.

Figure 9:
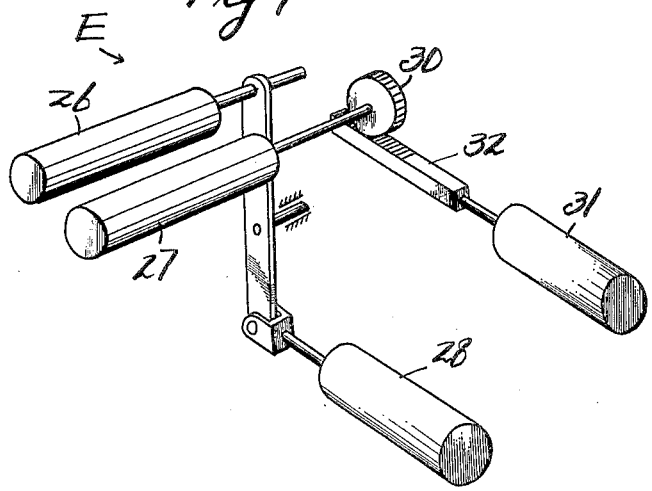
FIG. 9 is a perspective view of illustrative means for driving the breaking rollers at the breaking station.

Referring now to FIGS. 7 and 8, the breaking means or station E comprises two pairs of cotton feed rolls 22–25, inclusive, which are vertically arranged one above the other, and a pair of breaking rolls 26 and 27 are also positioned between the upper and lower cotton feed rolls 22–25 and adapted to be moved toward and away from each other. Thus, one breaking roll 27 is fixed in position while the other breaking roll 26 is mounted to be swung. When the continuous cotton fiber band 1 is fed by the cotton feed rolls 22, 23, 24 and 25, the movable breaking roll 26 is spaced apart by means of a cylinder 28, which is shown in FIG. 9, but when the feed movement is stopped, the breaking roll 26 will be brought into contact with the fixed breaking roll 27 by the cylinder 28. A gear wheel 30 will be then rotated by the piston rack 32 of a cylinder 31, whereby the two breaking rolls 26 and 27 are rotated in a counter direction by an amount necessary to break the fiber cotton 1, e.g. one-fourth of one complete revolution. Thus, the cotton fiber band 1 clamped between the upper cotton feed rolls 22 and 23 is torn off between the rolls 22 and 23 and the breaking rolls 26 and 27. While the upper cotton feed rolls 22 and 23 are positioned in closely adjacent relationship to each other to ensure that they clamp and feed the cotton fiber band 1 properly, the lower cotton feed rolls 24 and 25 are disposed more or less in spaced relationship from each other.

Rubber belts 33 and 34 are entrained around the cotton feed rolls 22–25 with two belts for each pair of upper and lower rolls being provided, one at the right side and the other at the left side. The rubber belts 33 and 34, as shown in FIG. 8, are positioned so as to lightly hold the cotton fiber band 1 on both sides and to prevent the cotton fiber band 1 on the released side from falling off after same has been broken. That is, the rubber belts 33 and 34, as shown in FIG. 7, are positioned in such a manner that the path of travel of the cotton fiber band 1 is downwardly diverging and the belts lightly contact the broken fiber cotton band 1 and prevent the falling of the individual cotton fiber bands 1 under their own weight. The clamping force exerted by the rubber belts 33 and 34 on the cotton fiber band 1 is so adjusted that when the spindle F' of the turret station F, which will be described more fully hereinafter, passes across the drooping cotton fiber band 1, the movement of the cotton fiber band 1 will be arrested by the spindle F' and easily carried away from the rubber belts 33 and 34. Fixed guides 35 and 36 are positioned adjacent the lower cotton feed rolls 24 and 25, respectively, as shown in FIG. 7. In addition, the fixed guides 35 and 36 are provided with notches 37 to clear the rubber belts 33 and 34, as shown in FIG. 8. The cotton feed rolls 22–25 and breaking rolls 26 and 27 are cantilever-wise journaled in a housing 38 and are opposed to the turret station F and are driven by driving means provided within the housing 38 in a manner to be later described. The fixed guides 35 and 36 are fixed on the outer wall of the housing 38. The withdrawing strings 2 attached to the cotton fiber band 1 are laterally sucked and retained by an extension of the suction nozzle 13 in the manner shown in FIG. 8.

Figure 11:
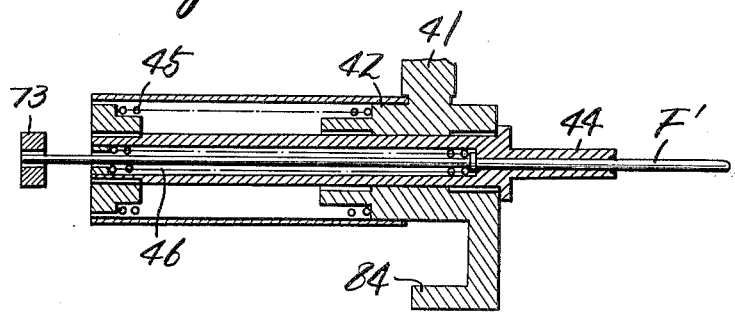
FIG. 11 is an enlarged sectional view of the spindle holding sleeve of the turret head station.

Referring now to FIG. 10, the turret machine or station F comprises a cruciform arm plate 40 fixedly mounted on a rotatable shaft 39, with arm rods 41 telescopically positioned in the cruciform arm plate 40 and holder sleeves 42 for the spindles F' being each fixed to the front end of one of said arm rods 41. The arm rods 41 are mounted within the cruciform arm plate 40 through springs 43 in such a manner that they are normally maintained in a retracted position. Each holder sleeve 42, as shown in FIG. 11, has a pusher 44 mounted therein and normally held in its retracted position by a spring 45. The pusher 44 is cylindrical in configuration and has the spindle F' slidably inserted therein and normally held in a projected position by a spring 46.

The turret machine F has four stations or positions, with its rotatable shaft 39 being intermittently rotated one-fourth of one complete revolution at a time. At the first position or station, winding means G are provided which is in fixed position. The winding means G is mounted below the breaking means E, hereinbefore described, and is provided with a fork 47 having two tines or bars associated with the spindle F' of the turret machine F. The fork 47, as shown in FIG. 12, is secured to the front end of a rotatable shaft 48 which is mounted in the housing 38 and is common to the breaking means E. The rotatable shaft 48 has a gear wheel 49 integrally mounted thereon and meshing with a gear wheel 50 which is fixed on a shaft 31, which is also provided with a pinion 53 meshing with a rack 52. The shaft 51 is rotatably positioned in brackets 54 and 55, and the rack 52 is slidably mounted on the guide 56, which is fixed to a portion of the housing 38. The rack 52 is connected to the front end of the piston rod 58 of a cylinder 57 by means of a bracket 59.

As the piston rod 58 of the cylinder 57 is projected and retracted, the rotatable shaft 48 will be rotated through the rack 52, pinion 53 and gear wheels 49 and 50, thereby resulting in a rotation of the fork 47. It is essential that the fork 47 be rotated through n complete revolutions, or an integral number of revolutions without any partial revolution occurring. A cylinder 60 serving to project and retract the fork 47 is connected to the rotatable shaft 48. Thus, the cylinder 60 is fixed to a portion of the housing 38, with a bracket being secured to the front end of a piston rod 61. The rotatable shaft 48, as described hereinbefore, is attached to the bracket 62. In addition, reference numeral 63 designates a slide positioned in the housing 38.

The fork 47 is normally maintained in a projected position but when the turret spindle F' reaches the winding station, the cylinder 57 will be actuated whereupon it will wind the individual cotton fiber articles formed by the breaking of the cotton fiber band 1 into suitable lengths, and upon completion of the winding the fork will be retracted. That is, the relation between the turret spindle F' and the fork 47 is such that, as shown in FIGS. 13 and 14, the turret spindle F' enters between the two tines of the fork 47. The assembly is so arranged that the axis of the turret spindle F' will be aligned with the axis of the rotatable shaft 48. As shown in FIG. 14, the turret spindle F' stops the individual cotton fiber articles which have been formed by breaking the continuous cotton fiber band 1 into suitable lengths by the breaking means E and enters between the two tines of the fork 47.

The cotton fiber band 1, after being broken into individual cotton fiber articles of suitable length by the breaking means E, as hereinbefore described, and each is lightly held between the rubber belts 33 and 34 and suspended so that the cotton crosses the path of travel of the turret spindle F'. Therefore, when the turret spindle F' is moved to the winding station, the cotton the fiber articles 1a are stopped by the turret spindle F' and inserted between the two tines of the fork 47. As the fork 47 is rotated under such circumstances, the cotton fiber articles formed from the cotton fiber band 1 will each be wound up as shown in FIG. 15. In addition, the reference numerals 63 and 64, as shown in FIGS. 13–15, designate cotton fiber article holding plates fixed to the housing 38.

On the other hand, the withdrawing string 2 is guided by a string guide 65 disposed adjacent one end of the cotton fiber article, as shown in FIGS. 13 and 16. The string guide 65 is bifurcated to guide the withdrawing string 2 from below the lower cotton feed rollers 24 and 25 to the center of the fork 47. When each of the cotton fiber articles are wound as a result of rotation of the fork 47, the string guide 65 aids in winding the withdrawing string 2 on the spindle F' at a position adjacent to one side of the fiber cotton 1.

As shown in FIGS. 17 and 18, the string embedding means or station H is the second station of the turret machine F and functions to embed the withdrawing string 2 in one end of the wound cotton fiber article 1a by the front end of a pusher 44. That is, the cotton backing plate 66 which is opposed to the spindle F' is placed in position so as to be movable by the actuation of a cylinder 67. The cylinder 67 is provided with a piston rod 68 whose front end is fixed to a main body 69, with a bracket 70 being provided in integral relationship on the cylinder 67. The bracket 70 is provided with a slide sleeve 71, with the slide sleeve having the cotton backing plate 66 fixed thereto. The slide sleeve 71 is slidably fitted over a guide rod 72 mounted between the housing 38 and the main body 69 and serves to move the cotton backing plate 66 upon actuation of the cylinder 67. A receiver member 74 associated with the rear end abutment portion 73 of the spindle F' is secured to the slide sleeve 71 and has a notched groove 74' through which the rear end abutment portion 73 of the spindle F' can pass.

When the spindle F' reaches the second station, the rear end abutment portion 73 enters the receiver member 74, and the wound cotton 1a on the spindle F' stops at a position opposed to the cotton backing plate 66. Actuation of the cylinder 67 causes the spindle F' and the wound cotton fiber article 1a to move toward the pusher 44, whereby the withdrawing string 2 wound on the spindle F' at the end of the wound cotton fiber article 1a is embedded in the end of the wound cotton fiber article 1a by the front end of the pusher 44.

As shown in FIG. 17, the compression shaping means or station I in the third position of the turret machine F comprises a depressing member 75 whereby the retainer sleeve 42 of the spindle F′, and which is supported by the cruciform arm plate 40 through an arm lever 41, is lowered to the compression shaping machine center, where first blades 76 and 77 are provided for vertically compressing the wound cotton 1a on the spindle F′, second blades 78 and 79 are provided for horizontally compressing the same, and pushers 44 and 80 are provided for compressing the wound cotton axially of the spindle F′.

Figure 19:
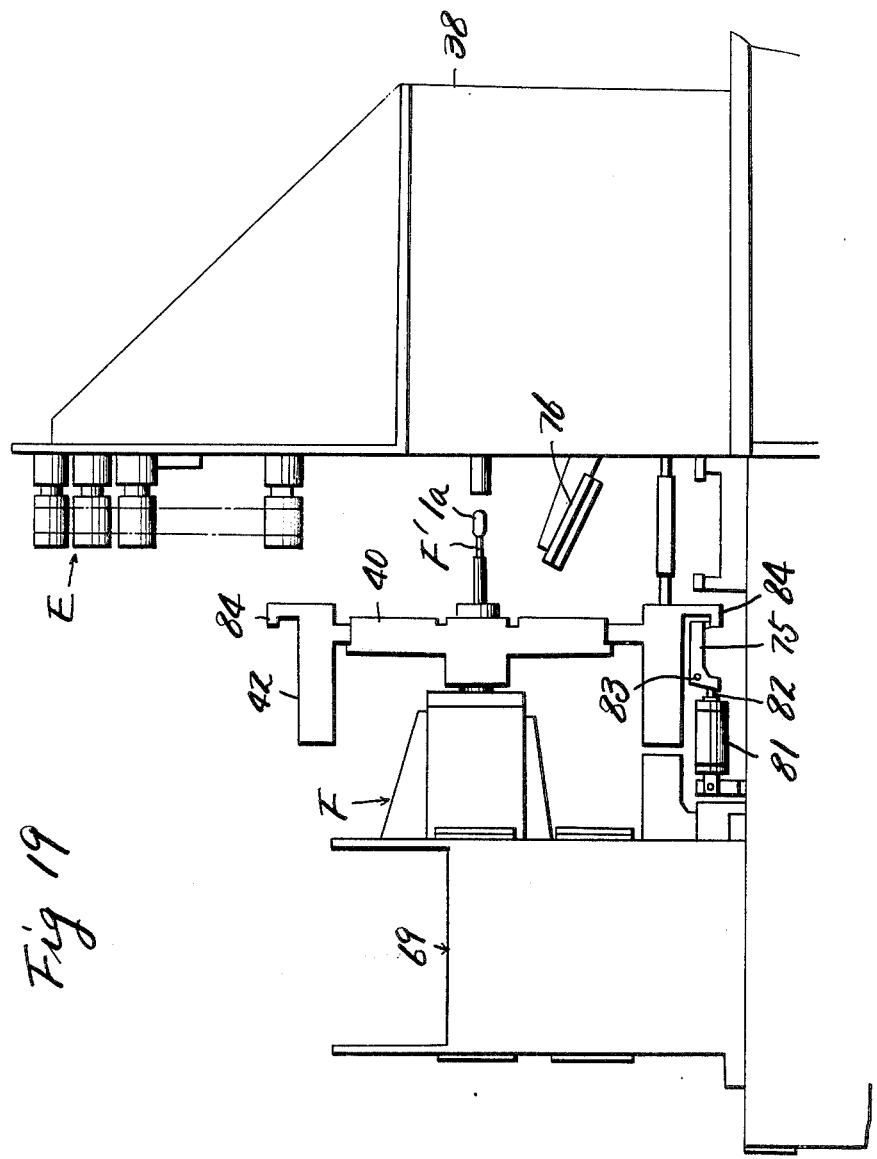
FIG. 19 is a fragmentary side view of the overall apparatus of the present invention.

The depressing member 75, as shown in FIG. 19, is in the form of an L-lever connected to the piston rod 82 of the cylinder 81, with the L-lever being capable of rotating around the axis of a pin 83. The L-lever is associated with the abutment portion 84 of the retainer sleeve 42 of the spindle F′. Therefore, when the spindle F′ reaches the third station, the abutment portion 84 of the retainer sleeve 42 is opposed to the depressing member 75, and upon actuation of the cylinder 81 depresses the spindle F′ along with the retainer sleeve 42 to the compressing shaping machine center.

Figure 20:
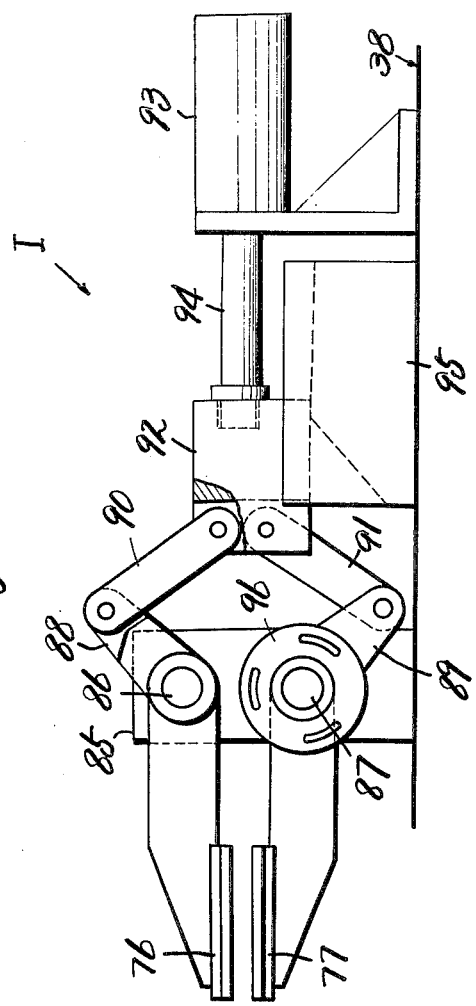
FIG. 20 illustrates a drive mechanism for the first blades of the compression shaping station of the apparatus of the present invention.

The first blades 76 and 77, as shown in FIG. 20, are fixed to the rotatable shafts 86 and 87 respectively, which are mounted on a bracket 85 on the housing 38 and which have levers 88 and 89 secured to their respective ends. The levers 88 and 89 are pin-jointed to a common slide block 92 through links 90 and 91 respectively. The slide block 92 is connected to the piston rod 94 of a cylinder 93 so that actuation of the cylinder 93 causes it to slide on a slide guide 95. The sliding movement of the slide block 92 causes the opening and closing movement of the first blades 76 and 77 around the axes of the rotatable shafts 86 and 87. In addition, at least one of the first blades has an attaching angle adjusting plate 96 secured thereto whereby the opening and closing angle of the first blades 76 and 77 can be adjusted.

Figure 21:
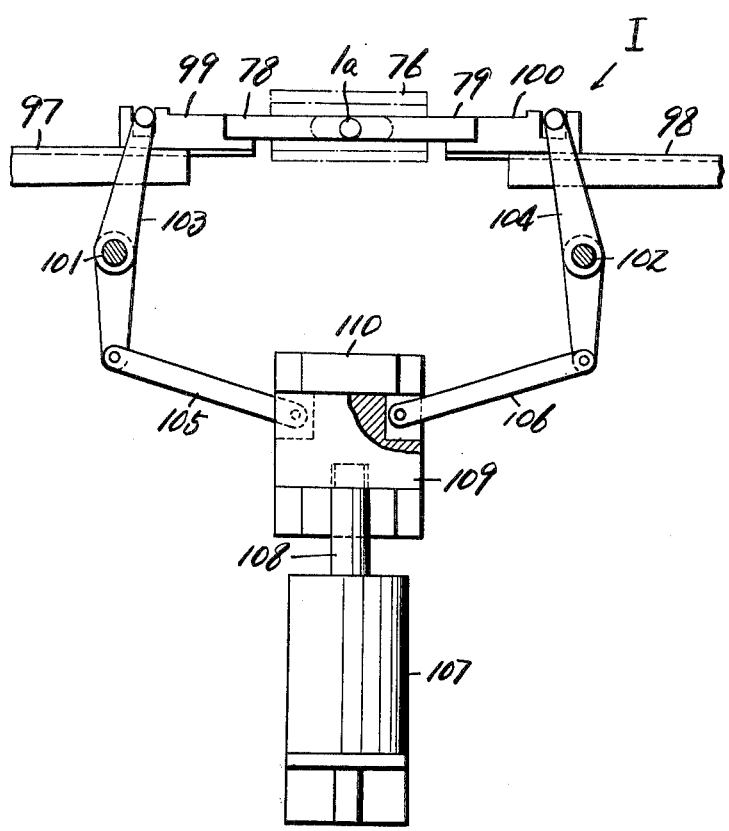
FIG. 21 shows a drive mechanism for the second blades of the compression shaping station.

The second blades 78 and 79, as shown in FIG. 21, are fixed to slide blocks 99 and 100, which are slidably mounted on slide guides 97 and 98 respectively. The slide blocks 99 and 100 are connected to one of the respective ends of levers 103 and 104, and which are rotatable around the axes of pivots 101 and 102, the levers having links 105 and 106 which are pin-jointed to the other ends thereof respectively. A common slide block 109 connected to the piston rod 108 of a cylinder 107 is pin-jointed to the other ends of the links 105 and 106 so that upon actuation of the cylinder 107 the slide block 109 slides on a slide guide 110. This movement will cause the second plates 78 and 79 to move toward and away from each other through the intermediary of the links 105 and 106 and the levers 103 and 104. The front ends of the second blades 78 and 79 are semi-circular and are adapted to clamp the wound cotton fiber article 1a which has been compressively shaped vertically by the first blades 76 and 77 and horizontally compressively shaped by the same to impart a columnar shape thereto.

Figure 22:
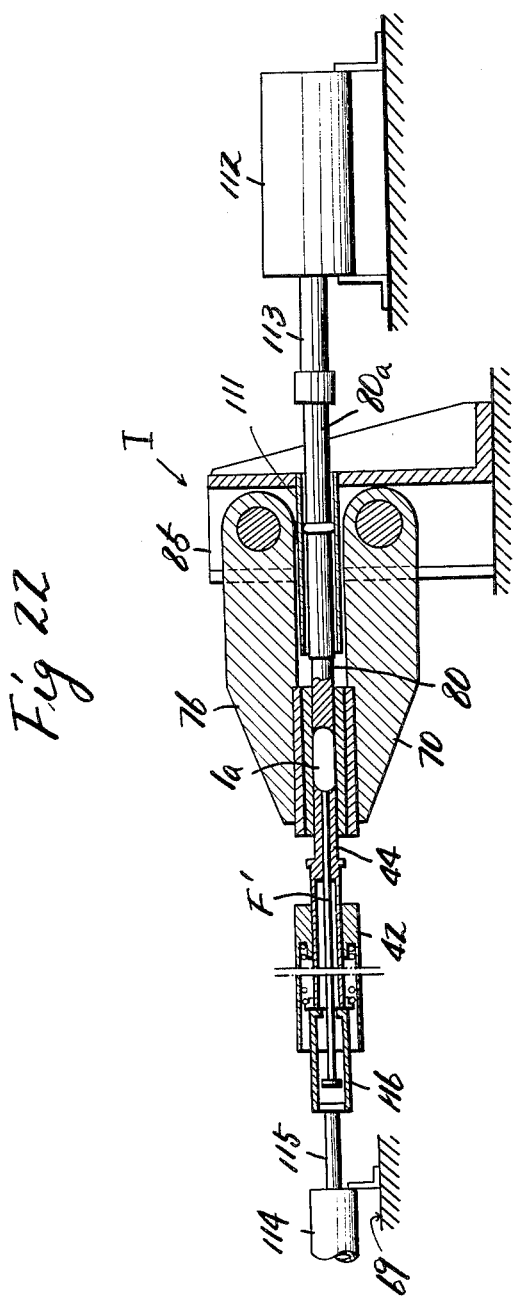
FIG. 22 shows drive mechanisms for the pushers.

Of the pushers 44 and 80 serving to axially compress the wound cotton article 1a, one pusher 80 is arranged to pass between the first blades 76 and 77, as shown in FIG. 22. That is to say, a guide sleeve 111 is fixed in position so as to extend through the bracket 85 for the first blades 76 and 77, and the base portion 80a of the pusher 80 is slidably inserted in the guide sleeve 111. The rear end of the base portion 80a is connected to the piston rod 113 of a cylinder 112 where the actuation thereof will cause the pusher to project and retract. The front end of the pusher 80 is concaved in semi-spherical shape and is adapted to compressively shape one end of the compressively column-shaped wound cotton articles 1a to impart a semi-spherical convex shape thereto. The other pusher 44 has a cylindrical body outside the spindle F′ and is supported by a cruciform arm plate 40 of the turret machine F through a retainer sleeve 42. When the pusher 80 is projected, only the pusher 44 is pushed out through a bracket 116 at the front end of the piston 115 of the cylinder 114. The two pushers 44 and 80 are coaxial with each other and serve to compressively shape axially the wound cotton article 1a, the front ends of the pushers 44 and 80 being shaped semi-spherically in a concave configuration. The cylinder 114 is secured to the main body 69 and the bracket 116 at the front end of the piston rod 115 is positioned in the path of travel of the spindles F′. The bracket has a bifurcated portion through which the rear end of the spindle F′ comes in. When the piston rod 115 of the cylinder 114 is projected, the piston rod 115 pushes out only the pusher 44 toward the other pusher 80.

The operation of the compression shaping means I will now be described by reference to FIG. 17. When the spindle F′ reaches the third station, the depressing member 75 will be actuated to lower the spindle 19′ to the compression shaping machine center position. Then the first blades 76 and 77 are closed to vertically compress the wound cotton article 1a wound on the spindle F′. Subsequently, the second blades 78 and 79 are laterally moved toward each other to enter between the first blades 76 and 77 to compressively shape the wound cotton article 1a from the opposite sides thereof. Finally, the pushers 44 and 80 are so actuated as to provide a tampon 1b of predetermined columnar shape. Upon completion of the compression shaping, the operation is repeated but in reverse order until the spindle F′ is returned to its original position.

Figure 23:
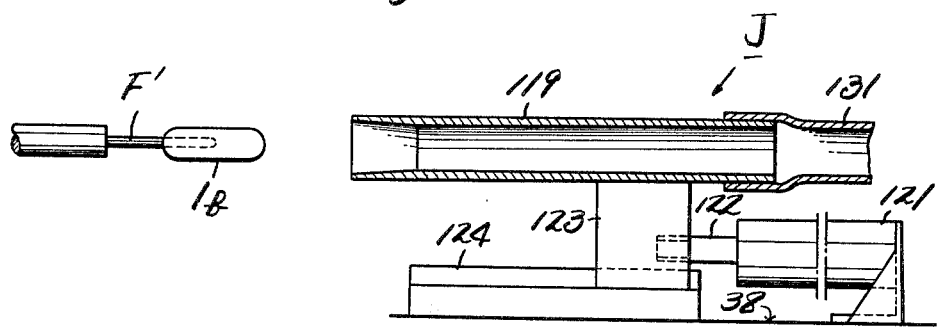
FIG. 23 is a side view of the discharge means for the finished tampon.

The discharge means J at the fourth station of the turret machine F, as shown in FIG. 17, comprises a movable chute 119 having tampon gripping pawls 117 and 118, and a withdrawing member 120 for the spindles F′. The movable chute 119, as shown in FIG. 23, is in the form of a cylindrical body adapted to receive the tampon 1b and is connected to the front end of the piston rod 122 of the cylinder 121 mounted in the housing 38 through the slide block 123, which is slidably mounted on a slide guide 124.

Figure 24:
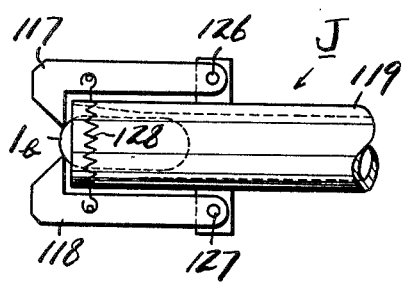
FIG. 24 is a plan view of a discharge chute for the finished tampon.
Figure 25:
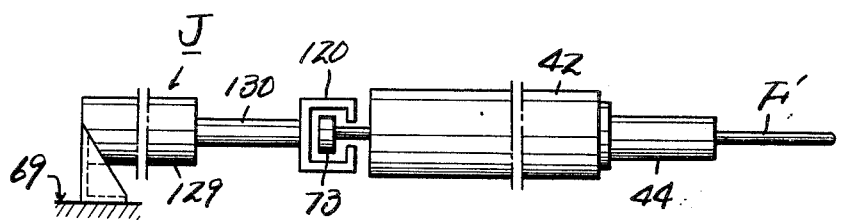
FIG. 25 is a side view of a spindle withdrawing mechanism.

The inner surface of the front end portion of the movable chute 119 is tapered to facilitate the gripping of a tampon 1b. Further, as shown in FIG. 24, the base portions of the tampon gripping pawls 117 at the front end portions thereof are openably and closably attached to the opposite sides of the movable chute 119 by means of pins 126 and 127. A spring 128 is positioned between the pawls 117 and 118 which functions to maintain the pawls 117 and 118 in a normally closed position. The front ends of the pawls 117 and 118 are hook-shaped and have their heads rounded. Thus, when the movable chute 119 is advanced, the tampon gripping pawls 117 and 118 are guided by the tampon 1b and are opened against the force of the spring 128 to grip the tampon 1b on the spindle F′. On the other hand, the withdrawing member 120 of the spindles F′, as shown in FIG. 25, is secured to the front end of the piston rod 130 of the cylinder 129 which is mounted on the main body 69, so that when the piston rod 130 is retracted, the withdrawing member 120 will engage the rear end abutment portion 73 of the spindle F' to withdraw the spindle. That is to say, the operation of the discharge means J is such that, first, the movable chute 119 is advanced to grip the tampon 1b on the spindle F', with the spindle F' being then withdrawn by the withdrawing member 120, and the movable chute being returned, after which the spindle R' is then returned to complete the discharging operation. At this time, the tampon 1b on the spindle F' has passed to the movable chute 119 since it has been removed from the spindle F'. In addition, a flexible tube 131 or the like is connected to the rear end of the movable chute 119 to deliver to completed tampons 1b to a reservoir or the like. The spindle F' from which the tampon 1b has now been removed is moved back to the first station to receive cotton fiber 1 thereon for winding.

Figure 26:
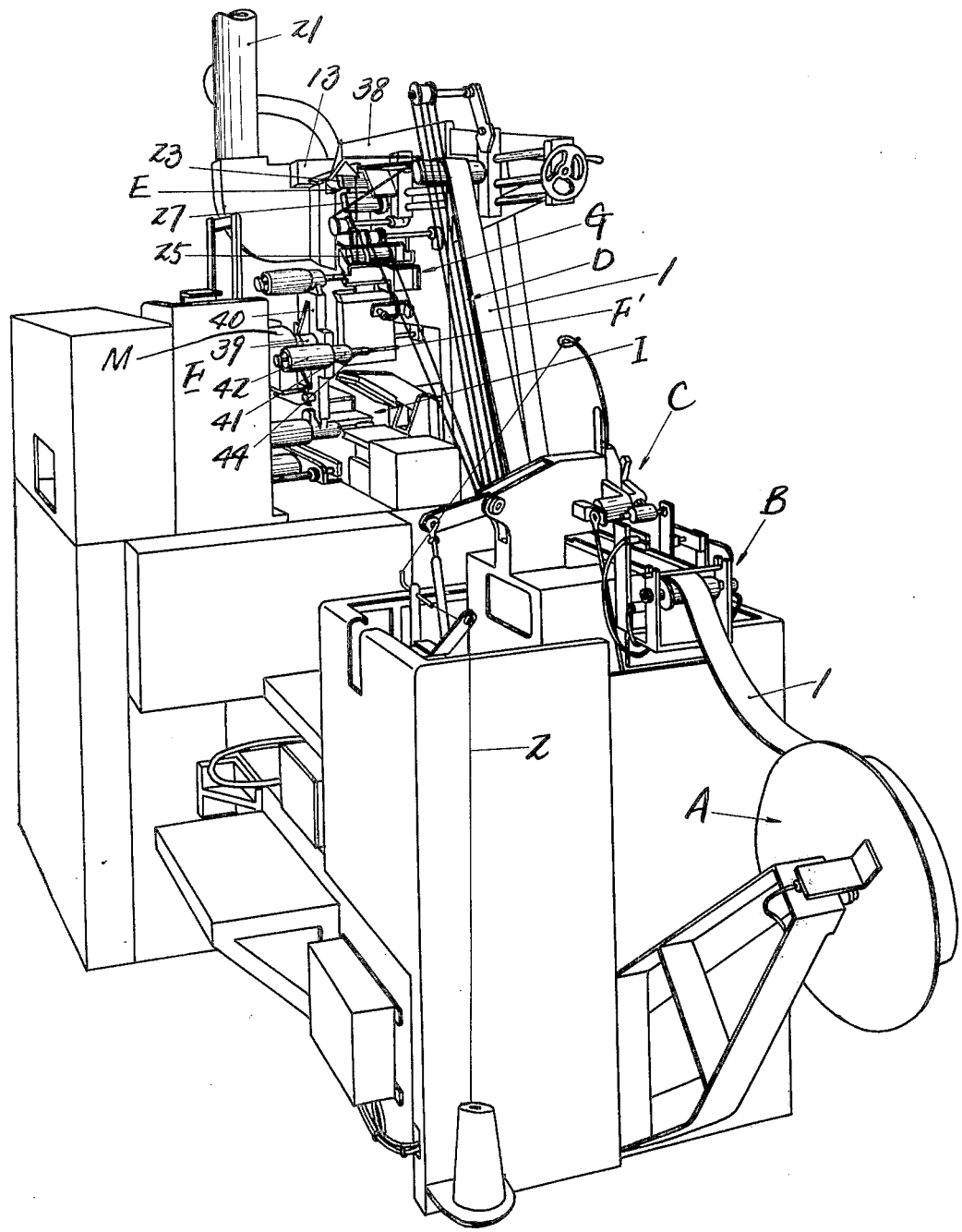
FIG. 26 is a perspective front view of all of the component stations making up the apparatus of the present invention assembled with one another in the form of a single machine.

As is illustrated in FIGS. 26 and 27, the various component parts or stations making up the apparatus of the present invention are shown in the form of a single unitary machine and the overall operation thereof is as follows. As shown in FIG. 26, reference letter M designates a motor for achieving the rotation of the turret spindle F to advance the turret spindle intermittently and sequentially through the four operational stages, as will be pointed out more fully hereinafter.

A continuous long cotton fiber band or strip 1 is intermittently drawn with a certain length being drawn at a time from the cotton reel A. This is accomplished by intermittently driving the cotton feed rollers. The cotton feed rollers are rotated in unison, each at the same number of revolutions, at the same peripheral speed by a common drive (not shown) through a chain, belt, or any other suitable transmission means. It is clear that the number of revolutions is to be adjusted to the necessary length of cotton fiber band 1 to produce a single tampon 1b. During the intermittent driving of the cotton feed rollers, that is to say, during the stoppage of the feeding of the cotton fiber strip or band 1, the string attaching station c is actuated to attach a withdrawing string 2 to the cotton fiber band 1. Thus, the desired withdrawing string 2 is attached to each length of cotton fiber band 1 that is required to produce a single tampon 1b. Further, during the stoppage of the feeding of the cotton fiber band 1, the breaking rollers of the breaking means E are actuated to break the cotton fiber band 1. This will result in the cotton fiber band 1 being broken into cotton fiber articles of certain predetermined lengths.

When the breaking of the cotton fiber band 1 has been completed to produce individual cotton fiber articles 1a, the turret machine F rotates the cruciform arm body 40 by one fourth of a revolution. This will cause the spindle F' to move to the first station from the last or final station and will stop the fiber cotton article 1a and transfer it to the winding means G. As soon as the rotation of the turret machine F is stopped, the driving of the cotton feed rollers is restarted and the individual stations of the turret machine F will also commence to perform their respective operations. In other words, the intermittent driving of the cotton fiber band 1 is effected during the stopping of the turret machine F. At the individual stations of the turret machine F, the following operations are carried out in unison. At the first station, the winding of the cotton fiber article 1a containing the withdrawing string 2 is carried out by the winding means G while at the second station, the embedding of the withdrawing string in one end of a wound cotton fiber article 1a is accomplished by the string embedding means H, and at the third station, the compression shaping of the wound cotton fiber article 1a is being carried out by the compression shaping means I, and finally, at the fourth station, the discharging of a finished tampon 1b is effected by the discharge means J.

Since the present invention is arranged in the manner described so far, it is possible to automatically and continuously produce tampons from long continuous cotton fiber band or strip, thereby greatly increasing the efficiency of operation, and to providing an extremely hygienic product without being touched by the hands of the operator. Moreover, since the cotton fiber strip or band is broken by being torn off, the sectional shape of the wound cotton can be made very smooth. Further, since the withdrawing string is embedded in one end of the product in a wound state, it can be easily withdrawn in use. Finally, the provision of a guide for the withdrawing strings obviates the danger of the withdrawing string becoming hooked in the course of production, thereby ensuring that the withdrawing string is wound and embedded in one end of the product.

While there have been described herein what are at present considered preferred embodiments of the several features of the invention, it will be obvious to those skilled in the art that modifications and changes may be made without departing from the essence of the invention. It is therefore to be understood that the exemplary embodiments thereof are illustrative and not restrictive of the invention, the scope of which is defined by the appended claims, and that all modifications that come within the meaning and range of equivalency of the claims are intended to be included therein.

We claim:

1. Apparatus, as a single unit, for producing menstrual tampons from a long continuous cotton fiber band comprising feeding means for feeding a long continuous cotton fiber band to said apparatus, said fiber band having a plurality of withdrawing strings incorporated therewith at spaced intervals therealong, a breaking station associated with said cotton fiber band withdrawing and feeding means for receiving the continuous cotton fiber band, said breaking station including means for breaking said continuous cotton fiber band into individual cotton fiber articles of a length corresponding to that generally of a finished tampon with each article containing a withdrawing string affixed thereto, a turret spindle mechanism spaced from said breaking station, said spindle mechanism having four spindle elements circumferentially spaced therearound, means associated with said breaking station for feeding, one at a time, the cotton fiber articles having a withdrawing string affixed thereto produced from the breaking of the continuous cotton fiber band to a spindle element at a fixed point on said turret spindle mechanism, a cotton fiber article winding station mounted on said apparatus in operative relationship with said turret spindle mechanism to form a first station which will be in operating registry with each spindle element, one at a time, said string embedding station including means to embed the withdrawing string of the cotton fiber article present on the spindle element in registry therewith and after the cotton fiber article present thereon has first passed through the first winding station, a cotton fiber article compressing station mounted on said apparatus in circumferentially spaced relationship to said string embedding second station and in operative relationship with said turret spindle mechanism to form a fourth station which will be in operating relationship with each spindle element, one at a time, said article discharge station including means to withdraw the cotton fiber article present on the spindle element in registry therewith as a finished tampon, and means for rotating said turret spindle mechanism to advance each of said spindle means intermittently and sequentially through said first winding station, said second embedding station, said third compressing station, and said fourth discharge station.

2. Apparatus in accordance with claim 1, wherein said breaking means for feeding the long continuous cotton fiber band include two pairs of feed rolls for intermittently advancing the long continuous cotton fiber band, and a pair of breaking rolls having means for bringing said breaking rolls into contact with one another and having means for breaking the cotton fiber band into cotton fiber articles of predetermined length when brought together and when the feed movement of the cotton fiber band has stopped, and taking them away from each other when the cotton fiber band is being advanced.

3. Apparatus in accordance with claim 1, wherein said winding station includes means suspending and supporting the cotton fiber article in the path of travel of the spindle element in registry therewith, a fork having rotating means positioned at the terminal end of the path of travel of the spindle element in registry therewith, winding guide plates disposed one above the other with said fork disposed therebetween, and a bifurcated string guide for guiding a withdrawing string through the winding station so that the withdrawing string may be wound on the spindle element at a position where it contacts the end of the cotton fiber element.

4. Apparatus in accordance with claim 1, said string embedding station including plate means for pressing the front end of the cotton fiber article wound on the spindle element in registry therewith, a cylindrical pusher supporting the rear portion of the spindle element and serving to push in and embed the withdrawing string carried at the rear end of the wound cotton fiber article, and a driving mechanism disposed between the winding station and the compressing station for actuating the plate means and cylindrical pusher.

5. Apparatus in accordance with claim 1, wherein said article discharging station includes means for advancement and retraction of the spindle element in registry therewith, spring means for normally holding the spindle element in its projected position, chute means adapted to advance and retract with respect to said spindle element whereby a tampon which has been compressively shaped into a predetermined configuration on a spindle element is grasped and fed into chute means when the chute means are advanced and said spindle element is withdrawn, and the tampon is removed from the spindle element when the chute means are retracted.

6. Apparatus in accordance with claim 1, wherein said apparatus further includes reel means adapted to receive a roll of continuous cotton fiber band thereon positioned in operative relationship with said cotton fiber band feeding means and a withdrawing string attaching station operatively associated with said apparatus, said attaching station including means for attaching the withdrawing string at spaced points on the cotton fiber band before advanced to the breaking station.

7. Apparatus in accordance with claim 6, wherein said withdrawing string attaching means include a guide wire forming a first string guide permitting the ends of the withdrawing strings attached to the cotton fiber band to be arrested by a second string guide, said second string guide having a pair of endless belts driven at the same speed as the cotton fiber band and a suction nozzle in association therewith, said first and second string guides and said suction nozzle being positioned along the path of travel of the cotton fiber band.

8. Apparatus for use in association with apparatus for producing menstrual tampons automatically comprising a turret spindle mechanism having four spindle elements circumferentially spaced therearound, means for feeding, one at a time, cotton fiber articles having a withdrawing string carried thereby to a spindle element at a fixed point on said turret spindle mechanism, a cotton fiber article winding station mounted on said apparatus in operative relationship with said turret spindle mechanism to form a first station which will be in operating registry with each spindle element, one at a time, said winding station including means to wind the cotton fiber article present on the spindle element in registry therewith, a cotton fiber article withdrawing string embedding station mounted on said apparatus in circumferentially spaced relationship with respect to the cotton fiber article winding station and in operative relationship with said turret spindle mechanism to form a second station which will be in operating registry with each spindle element, one at a time, said string embedding station including means to embed the withdrawing string of the cotton fiber article present on the spindle element in registry therewith and after the cotton fiber article present thereon has first passed through the first winding station, a cotton fiber article compressing station mounted on said apparatus in circumferentially spaced relationship to said string embedding second station and in operative relationship with said turret spindle mechanism to form a third station which will be in operating registry with each spindle element, one at a time, said cotton fiber article compressing station including means to compress the cotton fiber article present on the spindle element in registry therewith and after the cotton fiber article present thereon has first passed through the first winding station and the second embedding station, a cotton fiber article discharge station mounted on said apparatus in circumferentially spaced relationship to said article compressing third station and in operative relationship with said turret spindle mechanism to form a fourth station which will be in operating relationship with each spindle element, one at a time, said article discharge station including means to withdraw the cotton fiber article present on the spindle element in registry therewith as a finished tampon, and means for rotating said turret spindle mechanism to advance each of said spindle means intermittently and sequentially through said first winding station, said second embedding station, said third compressing station, and said fourth discharge station.

* * * * *